(12) United States Patent
Luna Pizarro

(10) Patent No.: US 8,409,201 B2
(45) Date of Patent: Apr. 2, 2013

(54) PERCUTANEOUS PATELLAR OSTEOSYNTHESIS SYSTEM APPLICABLE TO DISLOCATED PATELLA FRACTURES

(75) Inventor: Daniel Luna Pizarro, Delegación Miguel Hidalgo (MX)

(73) Assignee: Jose Adan Ortega Blanco, Zapopan, Jalisco (MX)

( * ) Notice: Subject to any disclaimer, the term of this patent is extended or adjusted under 35 U.S.C. 154(b) by 437 days.

(21) Appl. No.: 12/300,458

(22) PCT Filed: May 21, 2007

(86) PCT No.: PCT/MX2007/000062
§ 371 (c)(1),
(2), (4) Date: Nov. 11, 2008

(87) PCT Pub. No.: WO2007/148953
PCT Pub. Date: Dec. 27, 2007

(65) Prior Publication Data
US 2009/0216230 A1    Aug. 27, 2009

(30) Foreign Application Priority Data
Jun. 22, 2006 (MX) .................. PA/A/2006/007251

(51) Int. Cl.
*A61F 5/04* (2006.01)
(52) U.S. Cl. .............................. 606/54; 606/53; 606/57
(58) Field of Classification Search ............... 606/54–59
See application file for complete search history.

(56) References Cited

U.S. PATENT DOCUMENTS

| | | | |
|---|---|---|---|
| 5,810,827 A | 9/1998 | Haines et al. | |
| 5,968,051 A | 10/1999 | Luckman et al. | |
| 6,022,377 A | 2/2000 | Nuelle et al. | |
| 6,193,724 B1 | 2/2001 | Chan | |
| 6,287,307 B1 * | 9/2001 | Abboudi | 606/54 |
| 6,551,316 B1 * | 4/2003 | Rinner et al. | 606/57 |

(Continued)

FOREIGN PATENT DOCUMENTS

| | | |
|---|---|---|
| RU | 2 161 922 C1 | 1/2001 |
| WO | WO 97/34520 A2 | 9/1997 |

*Primary Examiner* — Eduardo C Robert
*Assistant Examiner* — Nicholas Plionis
(74) *Attorney, Agent, or Firm* — McDermott Will & Emery LLP

(57) ABSTRACT

The present invention relates to a percutaneous patellar osteosynthesis system applicable to any type of fracture of the knee cap, formed by two arms that contain two multidirectional movable securing devices for fitting to any type of knee cap, in which the arms close in a parallel manner by means of a scissors closure mechanism in order to keep the fragments confined and secured by means of a "zipper" based on manual compression. The devices for securing the knee cap have antero-posterior, up/down and also lateral mobility in order to mobilize the fractured fragments and to achieve a reduction and a satisfactory knee cap joint congruence. The arms have slidable guides for placing the implant in any required direction in order to keep the fragments stable, the guides slide on the arms and the parallelism sought in this type of fixing is achieved without having to be based on manual calculation, the latter customarily being used in broad tissue dissection. The system achieves reduction and internal fixing by means of a minimally invasive technique and less tissue damage. The system also has guides for fitting cerclage wiring on an implant of any configuration, facilitating reduction and fixing of patellar fractures and the taking of X-rays with the system in place.

16 Claims, 1 Drawing Sheet

U.S. PATENT DOCUMENTS 6,652,524 B1* 11/2003 Weiner ........................ 606/59
2003/0009167 A1 1/2003 Wozencroft
2006/0142777 A1 6/2006 Bastian
2006/0200127 A1* 9/2006 Ismail ........................ 606/59

* cited by examiner

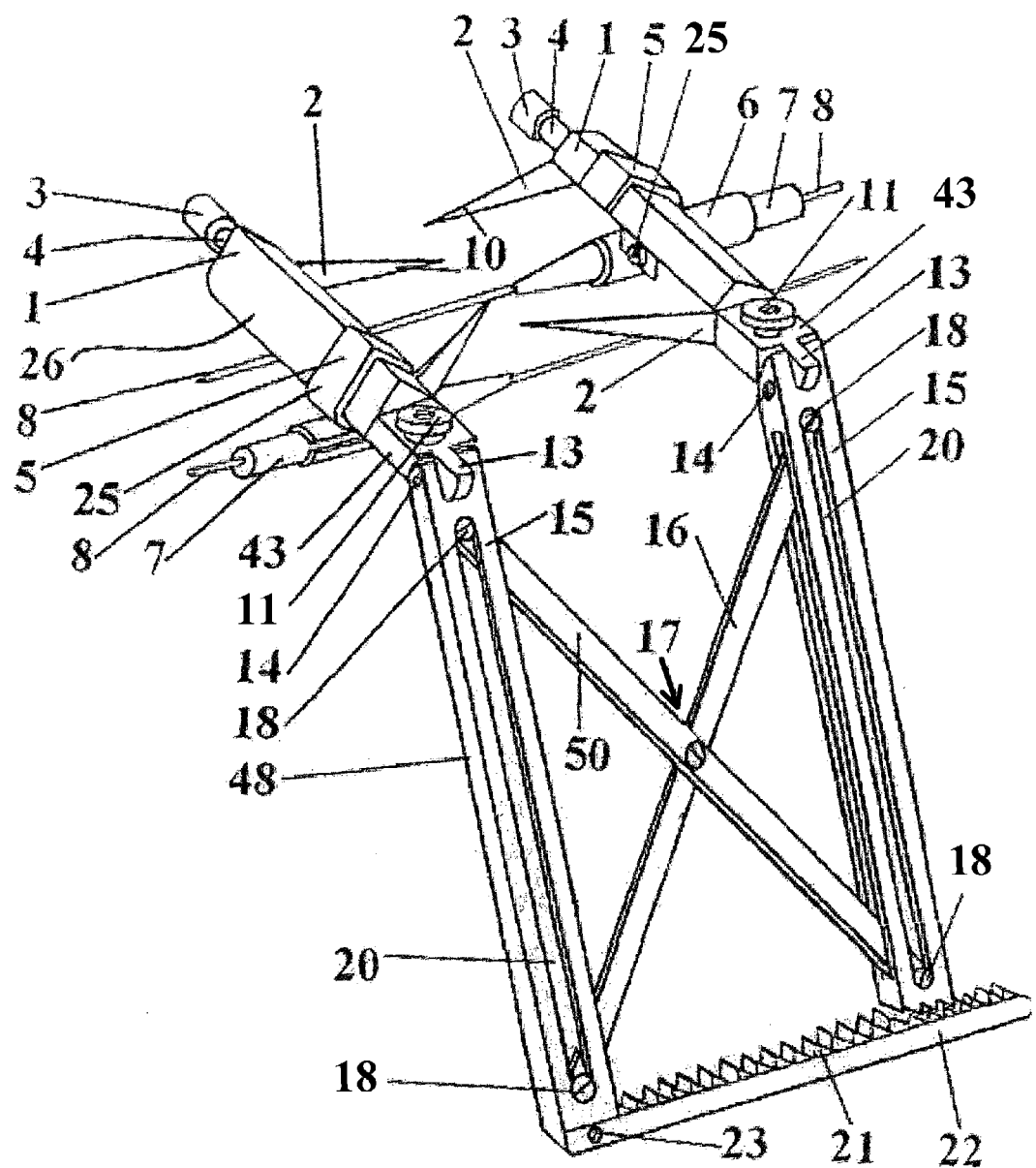

PERCUTANEOUS PATELLAR OSTEOSYNTHESIS SYSTEM APPLICABLE TO DISLOCATED PATELLA FRACTURES

TECHNICAL FIELD

The technical field of the present invention is mechanics, and more specifically osteosynthesis apparatus or systems that make it possible to correct fractures of dislocated kneecap.

BACKGROUND

There are several known ways to perform the percutaneous reduction of fractures and the placement of implants in fractures of the patella or kneecap but these maneuvers are manual or with instruments that are not suitable for keeping the fragments stable and this results from a technical difficulty that leads to the performance, as a better option, of an open reduction and the incision of the anterior tissues of the knee in order to reveal the fragments and place the implant according to a manual calculation determined by the individual skills of each surgeon because there are no guides for its more accurate placement; this lack of a device that allows the facilitation of surgical treatment in this pathology is reflected in the complications that occur in this type of surgery, which can appear in up to 47% including infections, fibrosis, ankylosis of the knee, pain due to irritation of the implant, failure to reduce the fragments, articular incongruity, inflammation due to prolonged duration of the surgery, and postoperative pain.

There is no system that accomplishes the maneuvers consisting of reduction and the placement of the implant with greater accuracy with a percutaneous technique in this type of pathology.

SUMMARY

As described in the present descriptive memorandum, the present invention relates to a system that makes it possible to place a more accurate implant, doing so with minimal dissection, in all types of fractures of dislocated patella or kneecap in knee surgery to repair the fractures and provide satisfactory articular congruity via a mechanism for the movement of several securing devices that it possesses. It consists of a manual parallel closure, four securing devices that make it possible to stabilize the fragments, and slidable guides with dynamic movements for the placement of any type of implant in any direction through the fragments of the fracture in order to enable the patient's rehabilitation and return to daily activities with greater speed and efficacy than other existing techniques with the goal of providing a rapid functional recovery.

The device is designed such that when it is actuated, the securing devices can immobilize the fragments and keep them stable, while in turn possessing a multidirectional movement mechanism for adjusting the articular surface and providing exact congruity without removing the system via external maneuvers. The system is placed by means of minimal incisions and a parallel closure is performed to reduce the fracture fragments, and the implant required by the fracture is placed with greater accuracy, parallel and with multidirectional options, as needed, through the bone tissue and the fragments to be treated via several slidable guides that make it possible to place in the patella any type of configuration that the surgeon appropriately creates according to the principles of internal fixation via a modified tension band and the variants thereof.

BRIEF DESCRIPTION OF THE DRAWING

FIG. 1 shows a perspective view of the system.

DESCRIPTION OF THE INVENTION

The characteristic details of this novel system are clearly shown in the following description and in an accompanying drawing, along with an illustration thereof and with the use of the same reference designations to indicate the parts and the FIGURE shown.

FIG. 1 shows a traditional view of the system, with the two main arms that show the parallel closure mechanism based on a movable cross-guide; the "rack" to maintain the closure; the two main arms with two movable securing devices each; and the guide on the arms for the placement of the implant in any direction.

The present system was designed for application in orthopedic knee surgery, is a tool that makes it possible to reduce, repair, and fix knee fractures of any configuration and place any currently known type of cerclage wiring, implant, or securing device for the fixation of knee fractures using a minimally invasive technique and without dissecting soft tissues, and reducing the postoperative comorbidity of an open reduction that makes a longer incision in the tissues and exhibits greater comorbidity during the postoperative period. The system according to the invention makes it possible to achieve compression of the fragments and keep them stable, and in turn, without removing the system, allows the reduction of the fracture to be manipulated mechanically and, if necessary, the correction of an articular incongruity of the surface of the knee cartilage. In turn, it has the characteristics of possessing, on the holding device arms, a slidable guide for the positioning of a longitudinally perforated rotating cylinder for the installation, via drilling, of Kirschner pins of any size oriented toward the fragments and through them in parallel form, thanks to the sliding of the guides in variable directions, which makes it possible to handle any size or type of kneecap with the security of placing the implant in a suitable direction and position. The four securing devices that hold the fracture fragments have their own mobility, which makes it possible to correct articular incongruities or manipulate the fragments without removing the system in order to reduce the fractures. With these characteristics the fragment technique is improved, the fragments are kept more stable, articular incongruities can be corrected, and in turn the implant can be placed more accurately, because the slidable guides place the implant accurately and not according to a manual calculation as is customarily done.

The system functions in the following way: Once a minimal incision approximately 5 mm long has been made in the lateral and base regions of the patella and the hematoma has been drained, the system is put in place with the holding arms open to their fullest extent; a "rack" is put into position that allows the parallel system to be closed but not opened unless the safety arm of the rack is removed; the system is put in place manually with the securing devices at the margin of the base of the patella and the other holding arm on the pole of the patella; and in the position of the pelvic extremity in extension the manual closure of the system is achieved; the fracture fragments are compressed; and, if necessary, the four securing devices (two for the base of the patella and two for the patellar pole) are calibrated according to the aperture diameter, because the securing devices are movable and adjusted to a patella of any size. Their size is calibrated and once the optimal size has been obtained the system is closed, the fragments of the patella are stabilized via the manual closure of the system, and palpation is performed with a blunt instrument, or an arthroscopic viewing device through the initial incision in order to confirm the articular congruity of the patella being treated; in the event of articular incongruity the securing devices on the holding base or on the pole are manipulated via a movable mechanical mechanism that the system possesses by means of a T-type Allen wrench and the articular congruity, if present, is corrected via the movements of the securing devices. Once the fragments have been manipulated to the surgeon's satisfaction, the implant is placed by means of the longitudinal drilling of the implant and through the fragments by means of the initial placement first of a slidable guide that is located on any securing arm of the patellar pole or base; the guide is slid until it reaches the proper site for the placement of the implant and, in turn, a calibrated "jacket" or "barrel" is placed for the installation of Kirschner pins as a guide or final implant in parallel form and in any direction, because the above-mentioned "barrels" have eccentric and parallel perforations along the longitudinal axis of the extensor apparatus so as to obtain broader coverage during the placement of the implant. The angular inclination of the system makes it possible to obtain an x-ray projection in order to confirm the articular congruity as well as the position of the implant, which can be placed via the guides in any configuration.

Turning now to the above-mentioned FIGURE, it can be seen that the system consists of two main arms (1) that may have a cylindrical, quadrangular, or circular form; this arm carries the sharp-pointed securing devices (2), which may have a cylindrical or prismatic form, two of which are present on each arm, which are oriented toward the center of the securing devices and which have a tip (10) that is inserted into the fracture fragments of the patellar pole and of the patellar base. These securing devices (2) may carry an upward-and-downward movement mechanism that can be manipulated mechanically via the rotation of an internal-thread system (4) by means of an Allen wrench, or the desired height of the securing elements can be manipulated via the rotation of the "thread" (11) that makes it possible to manipulate the fracture fragments and move them so as to achieve satisfactory reduction and articular congruity of the fragments and of the articular surface. The patellar securing devices (2) in turn may draw closer to each other on each arm in order to enclose any type or size of patella through manual manipulation or through an internal-thread system (4) that can be manipulated via the rotation of the knob (3) with these movements a kneecap of any size can be held. The holding arm (1) has a smooth sliding surface (26) that allows a "slidable guide" (5) to be displaced along the main arm on either side (1) the lower portion (25) of this guide has an articulated longitudinal hollow cylindrical form with multidirectional movement controlled by degrees (6) and whose longitudinal axis has an opening in order to be able to slide and to allow the installation of a Kirchner pin (8). This guide with its hollow cylinder in turn houses the slidable "jacket" or "barrel" (7) that has a cylindrical form and that is eccentrically perforated, in parallel and in different sizes, so that when it is rotated the installation of the guide pin will enjoy greater coverage from deep to superficial, from anterior to posterior, and for a kneecap of any type or size. When the implant is placed the guide slides and any number of perforations can be made parallel to the longitudinal axis of the patella. Both of the holding arms are terminated in a region (43) that may take the form of a movable hinge (13 and 14) affixed to the compression arms (48) that carry the parallel closure mechanism. This inclination allows transoperative x-rays to be taken, and also allows articular congruity and the placement of the implant to be checked.

The parallel manual closure mechanism consists of two main arms (48 and 15) that have a slot (20) along their longitudinal axis on each side, which slot has a "scissors" system (17) consisting of two arms (16 and 50) that are secured by a screw (18) that allows movement but not sliding through the slot (20) such that the closure mechanism is parallel and the closure is controlled by a toothed "rack" (22) that maintains the desired compression (21) and in turn has a joint (23) that can be unlocked in order to start a new compression. The materials' form and size are subject to variation provided that they do not compromise the mechanisms as described or an alteration of the essential nature of the function of the system. The system may be made of stainless steel with the standard for surgical instruments.

Percutaneous patellar osteosynthesis system, to reduce and fix fractures of the kneecap, includes two main arms that close the parallel system parallel by means of a scissors system, one part of which is fixed and whose other end is slidable, in order to keep the fracture fragments stable, with each arm containing two sharp-pointed securing devices whose purpose is to hold the fragments at two points each and that possess universal mobility in order to reduce the fragments and move them so as to achieve reduction and satisfactory articular congruity without removing the system, with the securing devices possessing mobility in order to hold a patella of any type or form or size and allowing the position to be modified via mechanical mechanisms that function manually or with a tool that enables rotation and functioning. It also contains guides on the said arms, which are slidable and provide proper guidance for the implant that is used for its optimal functioning, providing mobility and even more spatial coverage for any type of patellar thickness. The guides contain so-called "barrels" with various perforations for installing pins, cannulated screws, or any type of implant necessary in order to obtain a modified tension band and apply the biomechanical principle of converting the tension forces into compression. This system is characterized by the achievement of compression at four points, which makes it possible to obtain greater stability of the fragments in comparison with non-movable two-point compression clamps. The system also makes it possible to hold the fragments and obtain their reduction via the mechanical antero-superior and lateral movement mechanisms, along with independent variability of each securing device, which makes it possible to achieve 100% reduction and articular congruity, which is customarily achieved manually by releasing the holding mechanism every time an attempt is made to reduce the fragments. Once reduction is obtained without moving the system from its position, the system has the ability to seek the best direction for the implant within the patella, place the implant in a parallel position, if desired; modifying it in any direction via the cannulated guides that are used as a drilling guide, which guides can rotate in order to change the direction of the implant or pins, and thereby increase the range of coverage for the placement of the implant with no need to repeat the reduction. This reduction mechanism typically does not have any tools and because of the ease of its application it can be achieved under direct vision, palpation with blunt instruments, arthroscopic visualization, or through fluoroscopy, in order to achieve the articular congruity that is the ultimate goal, along with the stability of the fragments, through stabilization based on the placement of the implant. The securing devices for the patella also serve as a guide for fitting cerclage wiring in any desired configuration and strengthening the modified tension band.

Percutaneous patellar osteosynthesis system to reduce and fix fractures of the kneecap as described above, wherein the securing device (2) performs approaching motions between each one of the securing devices in order to encompass a patella of any type, form, or size, and moves in a direction toward the center of the closure and in an upward-and-downward and backward-and-forward direction in order to be inserted above the extensor apparatus of the patella and the contralateral in the patellar pole through the patellar extensor apparatus and more toward the anterior region of the patella, because this is the location of greater tension force of the extensor apparatus in the anterior third, with the holding of the arms having been designed to be located in the most anterior and superior portion of the main arm (26).

Percutaneous patellar osteosynthesis system to reduce and fix fractures of the kneecap as described above, wherein the slidable guide (5) has a part that is cylindrical, tubular, movable, and slidable in any direction manually if its position is determined, with a lateral slot in its longitudinal axis in order to house a cylindrical so-called "jacket" or "barrel" whose cylindrical portion penetrates the slidable guide, which "jacket" or "barrel" may have longitudinal perforations of varying diameters, depending on the implant to be utilized, and its course may be upwardly eccentric, which upon being rotated has a downwardly or laterally eccentric course allowing broader coverage during placement of the implant. This guide may have downwardly inclined eccentric perforations, such that upon rotation within the cylindrical part of the slidable guide the direction can change upwardly and laterally to the left or laterally to the right, depending on the manipulation, and thereby provide broader coverage during placement of the implant in the longitudinal direction.

Percutaneous patellar osteosynthesis system to reduce and fix fractures of the kneecap as described above, wherein the holding arms have a movable inclination so as to allow the articular surface to be viewed in a lateral projection via x-rays, fluoroscopy, or arthroscopy, and to enable confirmation of articular congruity and of the placement of the implant.

The invention claimed is:

1. A system for fixation of bone fractures, comprising:
    a securing portion for percutaneously securing fractured bone segments, the securing portion having first and second arms that extend in a parallel relationship with each other and are separated from each other by a distance, the securing portion having securing members that extend from the first and second arms and, when in use, engage and stabilize the bone segments; and
    a compression portion, coupled to the securing portion at a pivot joint, that adjusts the distance between the securing portion first and second arms, comprising
        a first arm rotationally coupled to one of the two parallel arms, the first arm having a longitudinal axis from a first end portion to a second end portion and a slot along the longitudinal axis;
        a second arm rotationally coupled to the other of the two parallel arms, the second arm having a longitudinal axis from a first end portion to a second end portion and a slot along the longitudinal axis; and
        a pair of guide members, each having a first end that adjustably resides within the first arm slot and a second end that adjustably resides within the second arm slot, the pair of guide members being coupled to each other and rotatable about a common axis when the guide member first ends or second ends are adjusted within the first or second arm slots;
    wherein the pair of guide members maintains a parallel relationship between the compression portion first and second arms and between the securing portion first and second arms when the distance between the securing portion first and second arms is changed; and
    wherein the securing portion extends substantially in a first plane and the compression portion extends substantially in a second plane, and wherein the securing portion is pivotable relative to the compression portion about an axis of the pivot joint such that the first plane is transverse to the second plane.

2. The system of claim 1, further comprising a first plurality of securing members extending from the securing portion first arm toward the securing portion second arm, each of the first plurality of securing members being coupled, at a first end, to the securing portion first arm and a second end being cantilevered between the securing portion first and second arms.

3. The system of claim 2, wherein the first plurality of securing members comprise a cylindrical or prismatic shape.

4. The system of claim 2, further comprising a second plurality of securing members extending from the securing portion second arm toward the securing portion first arm, each of the second plurality of securing members being coupled, at a first end, to the securing portion second arm and a second end being cantilevered between the securing portion first and second arms.

5. The system of claim 1, further comprising an adjustment mechanism on the securing portion first and second arms that adjusts positioning of the securing members.

6. The system of claim 1, further comprising a compression mechanism, coupled to at least one of the compression portion first and second arms, that secures a relative position between the compression portion first and second arms.

7. The system of claim 6, wherein the compression mechanism comprises a toothed rack.

8. The system of claim 1, further comprising a slidable guide, coupled to one of the securing portion first and second arms, the slidable guide being configured to carry a securing implant.

9. The system of claim 8, wherein the securing implant comprises a Kirchner pin.

10. A system for securing a fractured patella, comprising:
    a first arm having a securing portion and a compression portion, the securing and compression portions being rotatable relative to each other about a first joint axis, the first arm compression portion having a longitudinal axis from a first end portion to a second end portion and a slot along the longitudinal axis;
    a second arm having a securing portion and a compression portion, the securing and compression portions being rotatable relative to each other about a second joint axis, the second arm compression portion having a longitudinal axis from a first end portion to a second end portion and a slot along the longitudinal axis, the second arm being separated from the first arm by a distance;
    a plurality of securing members extending from the securing portion of at least one of the first and second arms toward the other of the first and second arms, each of the securing members being coupled to the securing portion at one end and a second end being cantilevered between the first and second arms, such that, when in use, the second end is configured to engage and stabilize the patella between the first and second arms; and
    a pair of guide members coupled to the first and second arms and that maintain a parallel relationship between the first and second arms when the distance between the first and second arms is changed, the guide members each having a first and second end, wherein the first ends each reside within the first arm slot and the second ends each reside within the second arm slot, the guide members being rotatable relative to each other about an axis;

wherein the securing and compression portions of the first arm extend in a first plane, the securing and compression portions of the second arm extend in a second plane, the first and second planes being substantially parallel, and the first and second joint axes being substantially coaxial.

11. The system of claim 10, further comprising a compression mechanism, coupled to at least one of the first and second arm compression portions, that secures a relative position between the first and second arms.

12. The system of claim 11, wherein the compression mechanism comprises a toothed rack.

13. The system of claim 10, wherein the plurality of securing members comprises two securing members extending from the securing portion of the first arm and two securing members extending from the securing portion of the second arm.

14. The system of claim 10, wherein the plurality of securing members comprise a cylindrical or prismatic shape.

15. The system of claim 10, further comprising slidable guides, coupled to the first and second arm securing portions, the slidable guides being configured to carry a securing implant.

16. The system of claim 10, further comprising adjustment mechanisms on the first and second arm securing portions that adjust positioning of the plurality of securing members.

* * * * *